United States Patent
Lim et al.

(10) Patent No.: US 7,686,814 B2
(45) Date of Patent: Mar. 30, 2010

(54) SYSTEMS AND METHODS FOR COMPRESSING AND DISTRACTING VERTEBRAE OF THE SPINAL COLUMN

(75) Inventors: Roy Lim, Memphis, TN (US); Arthur Conley, Edmond, OK (US); Anthony J. Melkent, Memphis, TN (US)

(73) Assignee: Warsaw Orthopedic, Inc.

( * ) Notice: Subject to any disclaimer, the term of this patent is extended or adjusted under 35 U.S.C. 154(b) by 1621 days.

(21) Appl. No.: 10/885,265

(22) Filed: Jul. 6, 2004

(65) Prior Publication Data

US 2006/0009777 A1 Jan. 12, 2006

(51) Int. Cl.
*A61B 17/58* (2006.01)
*A61B 17/60* (2006.01)
*A61F 2/00* (2006.01)

(52) U.S. Cl. ...................... 606/105; 606/279
(58) Field of Classification Search .................. 606/61, 606/86, 105, 246–279, 86 A, 86 R; 81/300, 81/343, 411, 413, 486
See application file for complete search history.

(56) References Cited

U.S. PATENT DOCUMENTS

| | | | |
|---|---|---|---|
| 49,424 A * | 8/1865 | Linsey | 81/413 |
| D111,907 S * | 10/1938 | Rue | D8/84 |
| 2,333,033 A | 10/1943 | Mraz | |
| 4,926,849 A | 5/1990 | Downey | |
| 5,167,662 A | 12/1992 | Hayes et al. | |
| 5,290,312 A | 3/1994 | Kojimoto et al. | |
| 5,439,463 A | 8/1995 | Lin | |
| 5,443,515 A | 8/1995 | Cohen et al. | |
| 5,540,687 A | 7/1996 | Fairley et al. | |
| 5,700,263 A | 12/1997 | Schendel | |
| 5,910,141 A * | 6/1999 | Morrison et al. | 606/61 |
| 5,928,231 A | 7/1999 | Klein et al. | |
| 6,019,020 A * | 2/2000 | Liou | 81/407 |
| 6,090,113 A | 7/2000 | Le Couedic et al. | |
| 6,113,600 A | 9/2000 | Drummond et al. | |
| 6,126,660 A | 10/2000 | Dietz | |
| 6,332,887 B1 | 12/2001 | Knox | |
| 6,530,929 B1 | 3/2003 | Justis et al. | |
| 6,648,891 B2 | 11/2003 | Kim | |
| 2001/0047172 A1 | 11/2001 | Foley et al. | |
| 2002/0128659 A1 | 9/2002 | Michelson | |
| 2003/0073998 A1 | 4/2003 | Pagliuca et al. | |
| 2003/0167059 A1 | 9/2003 | Young | |
| 2003/0187453 A1 | 10/2003 | Schlapfer et al. | |
| 2003/0236529 A1* | 12/2003 | Shluzas et al. | 606/105 |
| 2004/0024411 A1* | 2/2004 | Newton et al. | 606/105 |
| 2004/0117019 A1 | 6/2004 | Trieu et al. | |

FOREIGN PATENT DOCUMENTS

WO    WO 03/028566    4/2003

* cited by examiner

*Primary Examiner*—Thomas C Barrett
*Assistant Examiner*—Andrew Yang (57) ABSTRACT

Spinal surgical systems include a compressor mountable to a first vertebra and positionable relative to a fulcrum mountable to a second vertebra. The compressor and fulcrum are manipulated relative to one another to compress the first and second vertebrae. The systems further include a distractor mountable to a first vertebra and positionable relative to a fulcrum mountable to a second vertebra. The distractor and fulcrum are manipulated relative to one another to distract the first and second vertebrae.

35 Claims, 11 Drawing Sheets

SYSTEMS AND METHODS FOR COMPRESSING AND DISTRACTING VERTEBRAE OF THE SPINAL COLUMN

BACKGROUND

Orthopedic devices such as spinal rods, plates, tethers, staples and other devices can be secured along the spinal column between one or more vertebral levels to stabilize the one or more vertebral levels. While surgical procedures along the spinal column for placement of such devices are becoming less invasive, the decrease in space available in the approach to the surgical site and at the surgical site for handling and manipulating of the devices increases the difficulty in maneuvering, maintaining and finally positioning of the devices during the procedure. Furthermore, the ability to manipulate the vertebrae of the spinal column by compressing or distracting the vertebrae before attachment of the orthopedic devices is hindered by the construct attached to the vertebrae, the complexity and size of the footprint of the instruments involved in delivering the compression or distraction forces, the desire to maintain a minimally invasive approach to the spinal column, the vital anatomical structures adjacent the surgical site, and other factors.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

Systems for applying compression and distraction to vertebrae of the spinal column include, in one embodiment, a compressor mountable to a first vertebra and a fulcrum mountable to a second vertebra. The compressor includes an elongated body having an intermediate opening to receive an elongated shaft of the fulcrum therethrough such that when assembled the compressor and fulcrum have a nested configuration where their longitudinal axis cross one another at a location between their distal and proximal ends. Compression of the vertebrae is performed by moving the proximal ends of the compressor and fulcrum toward one another, which moves the distal ends of the compressor and fulcrum toward one another. The body of the compressor contacts the shaft of the fulcrum along a leverage surface adjacent the opening of the compressor, allowing the compressor to be leveraged with the fulcrum.

In another embodiment, a system includes an elongated compressor and an elongated fulcrum, which are positionable independently of one another through an operative approach to first and second vertebrae. The fulcrum and compressor are mountable to respective ones of the first and second vertebrae. The compressor and fulcrum are configured to nest with one another so that the compressor can be leveraged with the fulcrum to deliver a compression force between the first and second vertebrae.

In another embodiment, a system includes a distractor having an elongated body with a distal end mountable to a first vertebra, and a fulcrum having an elongated shaft with a distal end mountable to a second vertebra. The distractor includes a proximal handle portion and distal portion that is angled relative to the proximal portion away from the fulcrum when each is mounted to the respective vertebra. The distractor includes a leverage surface between the proximal handle portion and the distal angled portion that is positionable against the fulcrum such that at least the proximal ends of the distractor and fulcrum are separated from one another. The proximal ends of the distractor and fulcrum are moveable toward one another to move the distal ends of the distractor and fulcrum away from one another to distract the vertebrae. A mechanical advantage is provided by leveraging the distractor with its leverage surface against the shaft of the fulcrum.

In another embodiment, a system includes an elongated distractor and an elongated fulcrum, which are positionable independently of one another through an operative approach to first and second vertebrae. The fulcrum and distractor are separately mountable to the first and second vertebrae. The distractor and fulcrum are configured to act upon one another so that the distractor can be leveraged off of the fulcrum to deliver a distraction force between the first and second vertebrae.

In one embodiment, the distal end of the compressor or distractor is mountable to an anchor engaged to the first vertebra, and the distal end of the fulcrum is mountable to an anchor engaged to the second vertebra. A connecting member extends between the first and second anchors, and is secured between the anchors when the desired compression or distraction has been obtained. The connecting member can be a rod, plate, staple, flexible member or other suitable device positionable to extend between vertebrae and engageable to the vertebrae.

The systems can be employed in minimally invasive approaches to the vertebrae. In one embodiment, the minimally invasive approach is provided by a tubular retractor inserted through the tissue to provide a protected passageway to the first and second anchors. In a further embodiment, the tubular retractor is expandable to increase the size of the working space adjacent the first and second vertebrae relative to the size of the incision through which the retractor is inserted. In another embodiment, the approach is provided by one or more retractor blades inserted through the incision to provide a pathway to the first and second vertebrae. In another embodiment, the systems are employed directly through the tissue through one or more micro-incisions. In another embodiment, the first and second vertebrae are exposed in an open surgical technique and the systems are employed through the incision and retracted tissue providing the open approach.

The first and second vertebrae can be adjacent vertebrae of the spinal column, or can be vertebrae separated from one another by one or more intervening vertebrae. The approach to the vertebrae can be anterior, posterior, lateral, oblique, postero-lateral, or any other suitable approach. The first and second vertebrae can be located along any one or combination of regions of the spinal column, including the cervical, thoracic, lumbar and sacral regions.

Figures 1, 2:
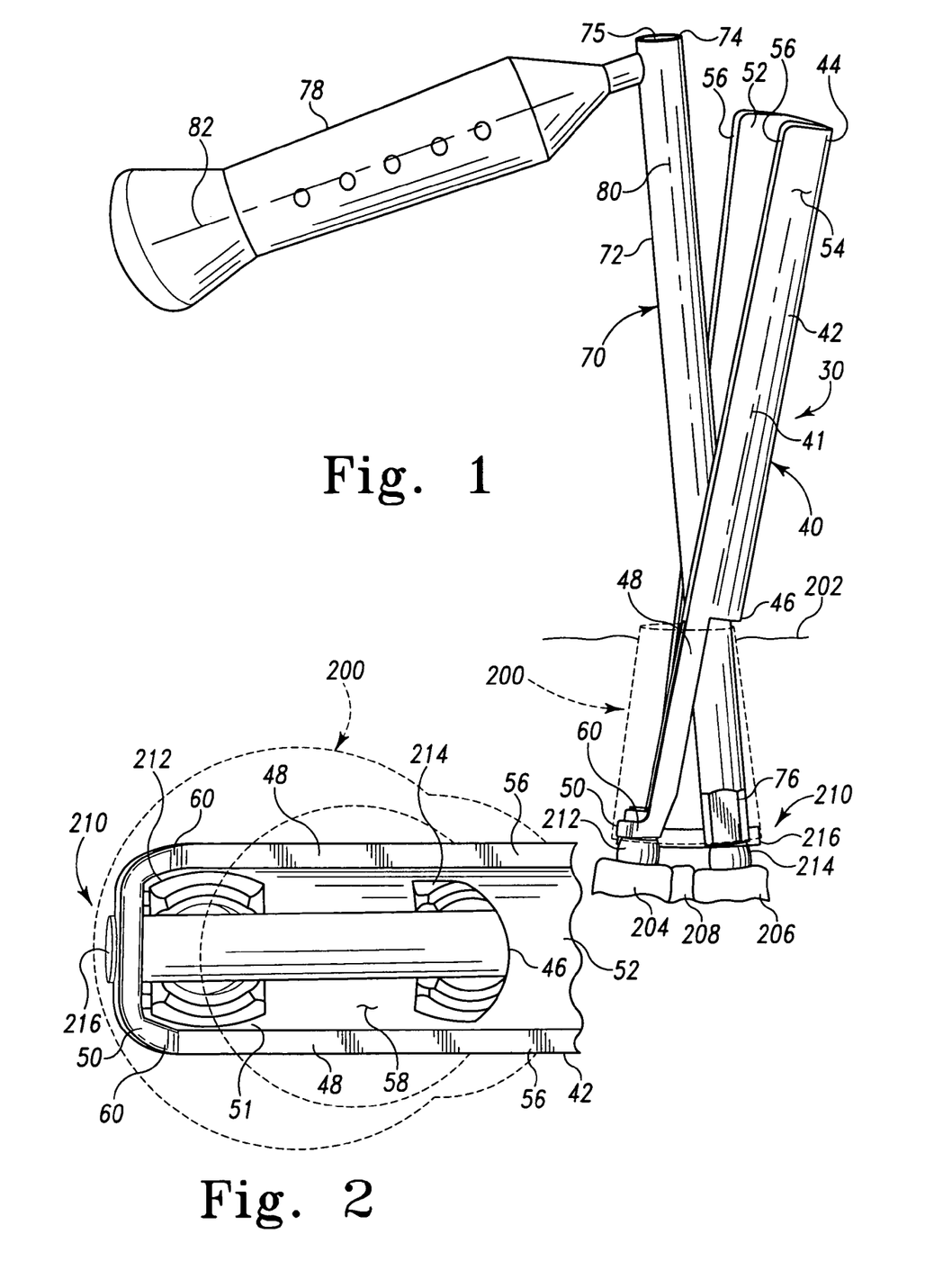
FIG. 1 is a view of a compression system positioned through a portal and mounted to a construct engaged to the spinal column.
FIG. 2 is a top view of the portal and construct of FIG. 1 showing a compressor of the compression system inserted through the portal and mounted to an anchor.

Referring to FIG. 1 therein shown a minimally invasive access portal 200 positioned through skin and tissue 202. Access portal 200 provides a pathway to the spinal column, including first vertebra 204 and second vertebra 206 and spinal disc space 208 therebetween. In the illustrated embodiment, access portal 200 is an expandable tubular retractor such as is described in U.S. Patent Application Publication No. 2003/0191371 A1, which is incorporated herein by reference. The expandable tubular retractor provides a portal that defines a protected passageway to the spinal column. The tubular retractor includes a first insertion configuration in which the retractor is cylindrical and is moveable in situ to a second configuration in which the distal end of the retractor is enlarged to form a proximally tapered working channel between the distal and proximal ends of the retractor. However, as discussed above, any suitable instrument, technique, or retractor for accessing the spinal column is contemplated.

In addition, vertebrae 204, 206 need not be directly adjacent vertebrae, and can be separated by one or more other vertebrae.

A construct 210 is engaged to vertebrae 204, 206 and extends therebetween. In the illustrated embodiment of FIG. 1, construct includes a first anchor 212 engaged to first vertebra 204, a second anchor 214 engaged to second vertebra 206, and a connecting member 216 extending between first and second anchors 212, 214. Anchors 212, 214 can be multi-axial type screws with a first portion (not shown) including a screw member threadingly engageable to the respective vertebra, and a second portion with a receiver member pivotally mounted to an enlarged head of the screw member. Connecting member 216 is an elongated rod received in passages of the receiver members of the anchors. The rod can be secured in the receiver members with a plug that is engaged to respective ones of the receiver members to firmly seat the rod against a bottom surface of the receiver member.

Other forms for the construct are contemplated. For example, the anchors can be uni-axial screws, bolts, hooks, staples, spikes, interbody devices, fusion devices or cages, artificial disc devices, or other suitable structure including a first portion for engaging one or more vertebrae and a second portion for engaging the connecting member. The connecting member can be a plate, strut, tether, staple, spacer or other suitable device for extending between two or more anchors. Furthermore, the construct can be arranged to extend between more than two vertebrae, and can be engaged to three or more anchors. The plug can be a set screw, cap, or other device that engages the construct to the anchor.

FIGS. 1-6 show a compressor system 30 that is mountable to vertebrae 204, 206 and manipulatable relative thereto to deliver a compressive force between vertebrae 204, 206. When the desired compression force has been applied, construct 210 is secured between vertebrae 204, 206 to maintain the compression post-operatively. In the illustrated embodiment, system 30 is mountable to anchors 212, 214 engaged to respective ones of the vertebrae 204, 206. It is also contemplated that system 30 can be mounted directly to vertebrae 204, 206; or mounted to a secondary fastener or device engaged to vertebrae 204, 206 which does not form a part of the construct 210.

System 30 includes a compressor 40 mountable to first vertebra 204. Compressor 40 includes an elongated body 42 extending along a longitudinal axis 41 between a proximal end 44 and a distally oriented leverage surface 46. A pair of arms 48 extends distally from body 42. Arms 48 define an opening 58 therebetween. An engaging member 50 is provided at the distal ends of arms 48 and extends between arms 48. As shown in FIG. 2, engaging member 50 is offset laterally relative to arms 48 by a pair of extensions 60 extending transversely to and laterally from respective ones of the arms 48 and an end member extending between extensions 60. Arms 48 and engaging member 50 form a receptacle 51 for receiving a portion of an anchor engaged to a vertebra therein. In the illustrated embodiment, receptacle 51 includes a generally rectangular shape that receives the receiver member of anchor 212 in a manner that prevents the receiver member from rotating relative to engaging member 50. Other shapes for receptacle 51 are also contemplated, including omitting receptacle 51, so long as engaging member 50 is capable of engaging an anchor or a vertebra.

Body 42 further includes opposing sidewalls 56 extending therealong, and a channel 52 extending between sidewalls 56. Channel 52 includes a U-shape formed by a concavely curved surface sized to receive elongated shaft 72 of fulcrum 70 therein; however, other shapes are also contemplated. Body 42 includes an outer surface 54 opposite channel 52 having a convex curvature to facilitate gripping of body 42. Outer surface 54 can also be non-curved, and include grip-enhancing features such as knurling, indentations, protrusions or the like.

Compression system 30 further includes a fulcrum 70 nestably positioned relative to compressor 40 and mountable to second vertebra 206. Fulcrum 70 includes an elongated shaft 72 extending along a longitudinal axis 82 between a proximal end 74 and a distal engaging member 76. Elongated shaft 72 defines a passage 75 extending therethrough. Handle 78 extends from proximal end 74 along a handle axis 80. Handle axis 80 is oriented transversely to longitudinal axis 82. In the illustrated embodiment, handle axis 80 is orthogonal to longitudinal axis 82; however, other transverse orientations are also contemplated. The transverse orientation of handle 78 facilitates maneuvering and gesturing of the fulcrum 70 through portal 200. The transverse orientation of handle 78 also maintains access to passage 75. In other embodiments, elongated shaft 72 does not include a passage 75, but rather is solid.

Figures 3, 4:
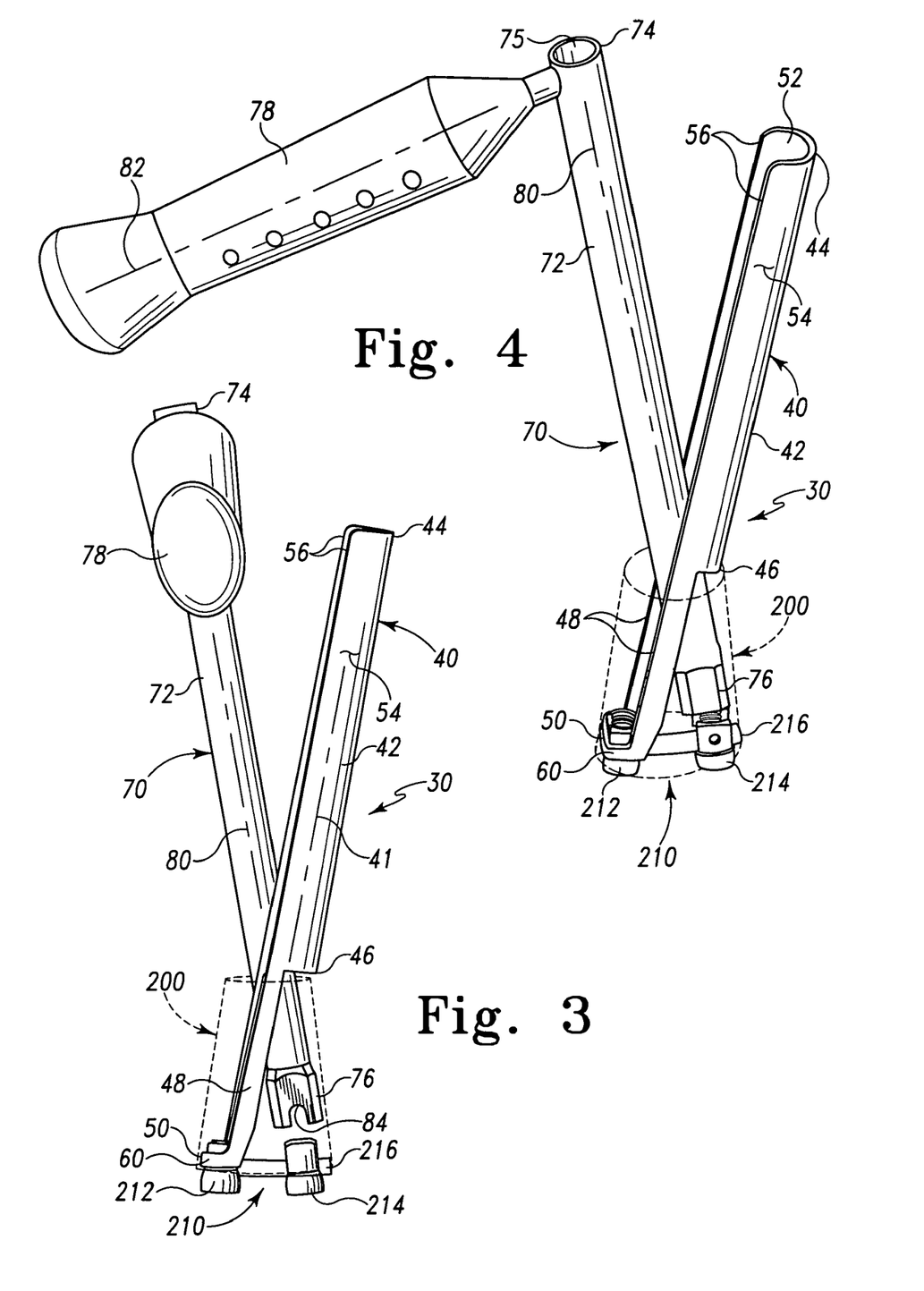
FIG. 3 is a view of the portal, construct and compressor of FIG. 2 with a fulcrum being positioned through the compressor.
FIG. 4 is a view showing the compressor and fulcrum in the portal and mounted to the construct before compression of the spinal column.
Figure 5:
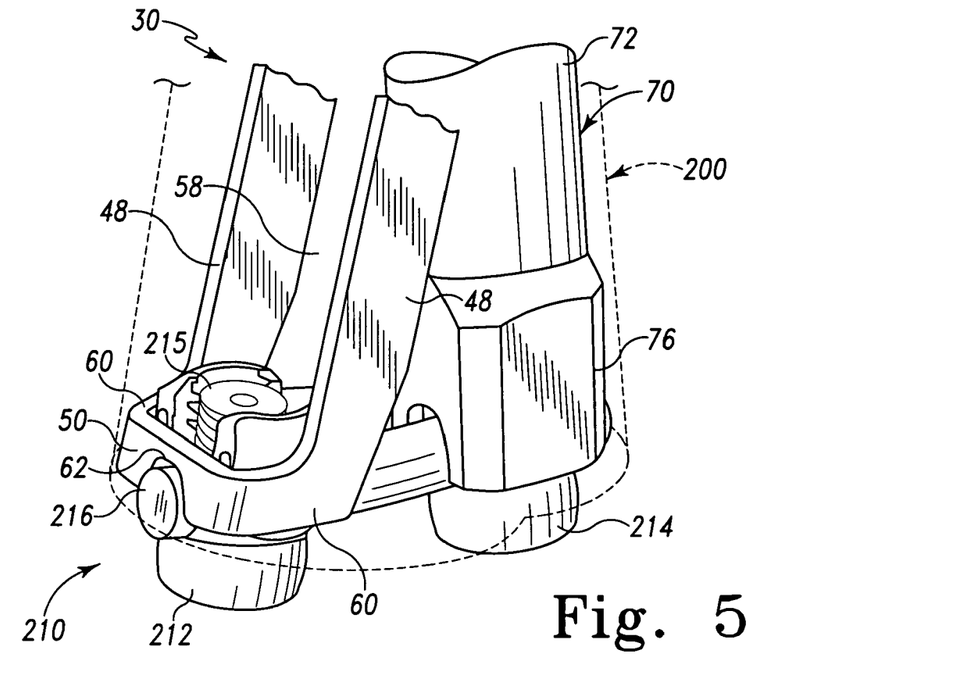
FIG. 5 is a view showing engagement of the distal portions of the compressor and fulcrum mounted with the construct before compression of the spinal column.

Passage 75 can extend through engaging member 76. Passage 75 includes a distally oriented opening in engaging member 76 that is structured to receive the receiver member of the anchor to which it is engaged therein. As shown in FIG. 3, the sides of engaging member 76 can be enlarged relative to the shaft 72 so as to extend about the head of the receiver members. Fulcrum 70 is oriented so that engaging member 76 can be positioned through opening 58 of compressor 40. In FIG. 4, fulcrum 70 is rotated 90 degrees about longitudinal axis 82 relative to its FIG. 3 orientation to align engaging member 76 with the receiver member of anchor 214. As shown in FIG. 5, engaging member 76 is positioned about the receiver member of anchor 214. The distal end of engaging member 76 includes a distally-oriented recess 84 (FIG. 3) formed therein to receive connecting element 216 therein when engaging member 76 is fully seated on the receiver member of anchor 214. The interface between engaging member 76 and the receiver member of anchor 214 can be configured so that fulcrum 70 cannot rotate relative to the receiver member of anchor 214, allowing the alignment of the receiver member relative to fulcrum 70 to be maintained during the procedure.

In use, access portal 200 is positioned to access the spinal column. Procedures can be performed in disc space 208 or on vertebrae 204, 206. Such procedures can include one or more of a discectomy, facectomy, laminectomy, artificial disc placement, fusion device placement, annulus repair or augmentation, or any other spinal surgical procedure. Anchors 212 and 214 can be engaged to respective ones of the vertebrae using any known instruments and techniques. Connecting member 216 can be positioned through access portal 200 and positioned in the receiver members of anchors 212, 214. Connecting member 216 is tightly secured to one of the anchors, such as anchor 212, with a plug engaged to the receiver member. The plug can be an internally or externally threaded set screw, nut, washer, cap or any other device or combination of devices capable of engaging the connecting member in, on, about or adjacent to the receiver member of the anchor. A second plug can also be positioned in the receiver member of the other anchor 214 to loosely retain connecting member 216 therein.

As shown in FIG. 2, compressor 40 is positioned about the receiver member of anchor 212. Opening 58 is aligned with the receiver member of anchor 214. In FIGS. 3 and 4, fulcrum 70 is delivered through portal 220 and opening 58 between arms 48 for engagement with anchor 214, as shown in FIG. 5.

When engaged to anchor 214, fulcrum 70 is manipulated and nestably positioned relative to compressor 40 for manipulation relative to one another to deliver a compressive force to vertebrae 204, 206. The nestable positioning maintains contact and alignment between compressor 40 and fulcrum 70 during compression of the spinal column.

In the illustrated embodiment, fulcrum 70 is received through opening 58 of compressor 40 such that shaft 72 and body 42/arms 48 cross one another. Thus, the longitudinal axes 82, 41 of fulcrum 70 and compressor 40 form an X-shape in their engaged positions with anchors 212, 214. Elongated shaft 72 of fulcrum 70 is positioned in contact with leverage surface 46 of elongated body 42, and channel 52 is oriented toward elongated shaft 72 of fulcrum 70. Connecting member 216 is received in recesses 62, 84 of engaging members 50, 76 of compressor 40 and fulcrum 70, respectively, when compressor 40 and fulcrum 70 are fully seated on the respective anchors. Recesses 62, 84 allow engaging members 50, 76 of compressor 40 and fulcrum 70 to be seated further distally on the receiver members of the anchors, providing a firm grip about the anchor to maintain engagement during compression of the spinal column.

Figure 6:
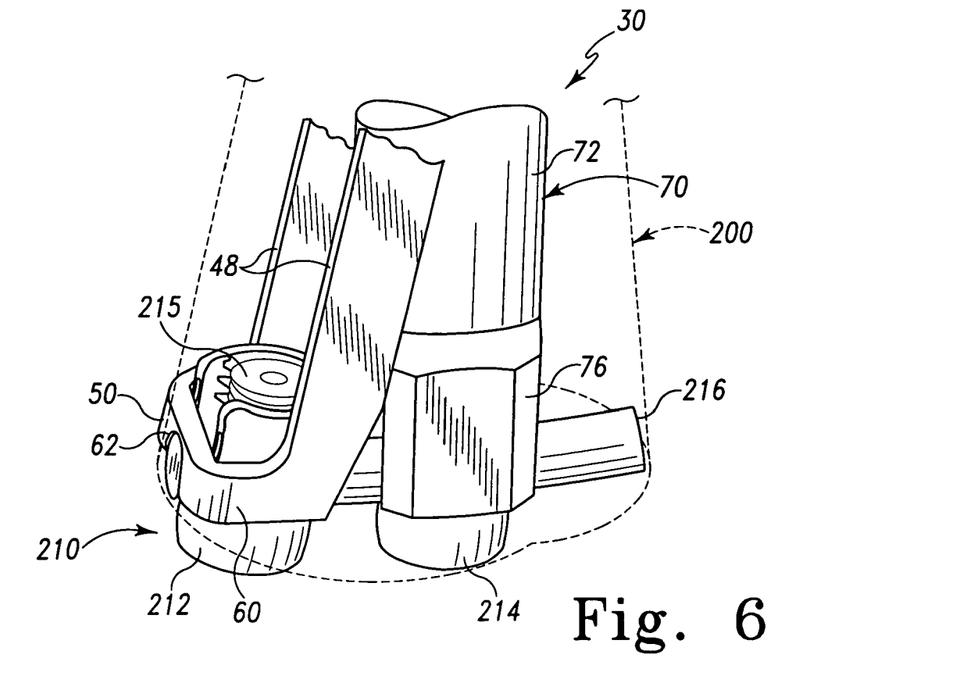
FIG. 6 is ad view showing engagement of the distal portions of the compressor and fulcrum mounted with the construct after compression of the spinal column.

To compress vertebrae 204, 206, the proximal ends 44, 74 of compressor 40, fulcrum 70 are moved toward one another. Compressor 40 pivots relative to fulcrum 70 due to the contact between leverage surface 46 and the outer surface of elongated shaft 72 of fulcrum 70. The location along elongated shaft 72 in contact with leverage surface 46 to effect pivoting of compressor 40 relative to fulcrum 70 can vary proximally and distally along shaft 72. The contact location can vary depending on the separation distance of anchors 212, 214, the alignment between vertebrae 204, 206, the orientation of portal 200 relative to vertebrae 204, 206, and the orientation of compressor 40 and fulcrum 70 relative to one another and to the anchors 212, 214. Accordingly, compression system 30 has application even when anchors 212, 214 are not aligned with another or spaced various distances from one another while still minimizing the footprint of system 30 through portal 200. As proximal ends 44, 74 are moved toward one another, the distal ends of fulcrum 70 and compressor 40 move toward one another, compressing vertebrae 204, 206 as shown in FIG. 6.

As compressor 40 and fulcrum 70 are moved toward one another, channel 52 of compressor 40 receives elongated shaft 72 of fulcrum 70. This nesting arrangement further provides a low profile footprint for compression system 30 through portal 200, allowing the size of portal 200 to be minimized. Furthermore, receipt of fulcrum 70 through opening 58 of compressor 40 provides a low profile footprint extending transversely to connecting member 216 since the longitudinal axes of compressor 40 and fulcrum 70 are aligned along the axis extending between the receiver members of anchors 212, 214.

With connecting member 216 secured tightly in anchor 212 with a plug, connecting member 216 moves relative to anchor 214 as the vertebrae are compressed, moving anchors 212, 214 toward one another. When the desired compression has been obtained, the plug or set screw provisionally engaged to anchor 214 can be tightened with a driver instrument positioned through passage 75 of fulcrum 70. Alternatively, a plug can be delivered through passage 75 of fulcrum 70 to engage the connecting member 216 to anchor 214. Fulcrum 70 can further function as a counter-torque as the plug is tightened in the receiver member against the connecting member. Handle 78 can be grasped to prevent the receiver member and/or the bone engaging portion of anchor 214 from rotating as the plug is tightened into position. When secured to anchors 212, 214, connecting member 216 can post-operatively maintain the compression applied with compressor 40 and fulcrum 70. Compressor 40 and fulcrum 70 can then be un-mounted from anchors 212, 214 and removed through portal 200.

Other embodiments contemplate other nestable arrangements between fulcrum 70 and compressor 40. For example, compressor 40 and fulcrum 70 can be provided with an nesting configuration in which compressor 40 and fulcrum 70 extend along side one another, and include portions that overlap and are contactable with one another along a leverage surface to effect pivoting of compressor 40 and fulcrum 70 relative to one another. In another example, one or more of the longitudinal axes of compressor 40 and fulcrum 70 are offset relative to the longitudinal axis of the connecting member extending between anchors 212, 214.

Figure 7:
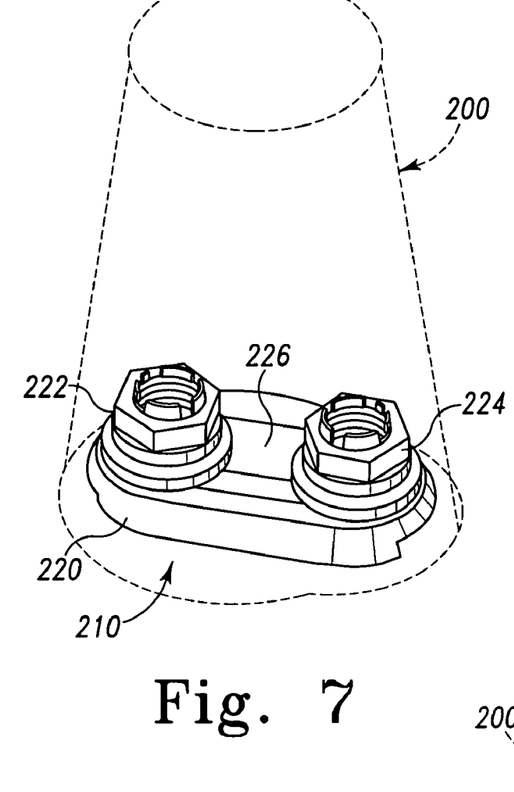
FIG. 7 is a view of the portal and another embodiment construct engaged to the spinal column.

Referring to FIGS. 7-14, there is shown another embodiment compression system 130 that includes a compressor 90 and a fulcrum 120 engageable to another embodiment construct 210. As shown in FIG. 7, construct 210 includes a first anchor 222 and a second anchor 224 engageable to first and second vertebrae, such as vertebrae 204, 206 discussed above. Each of the anchors 222, 224 includes a first portion (not shown) for engaging the vertebra. Anchors 222, 224 also include a second portion for securing the connecting member between the vertebrae. In the illustrated embodiment, the second portion is an enlarged head structure that clamps or secures the plate-like connecting member 220 to the respective vertebra. Connecting member 220 includes one or more central openings 226 through which anchors 222, 224 extend. The enlarged head structure of the second portion of the respective anchor bears against the upper surface of connecting member 220 to secure it to the respective vertebra. The head-like structure can be integrally formed with a threaded shaft or other body comprising the first anchor portion that is received through the central opening 226. The second anchor portion can also be, for example, a nut, cap or other device that engages connecting member 220 to an anchor.

Figure 8:
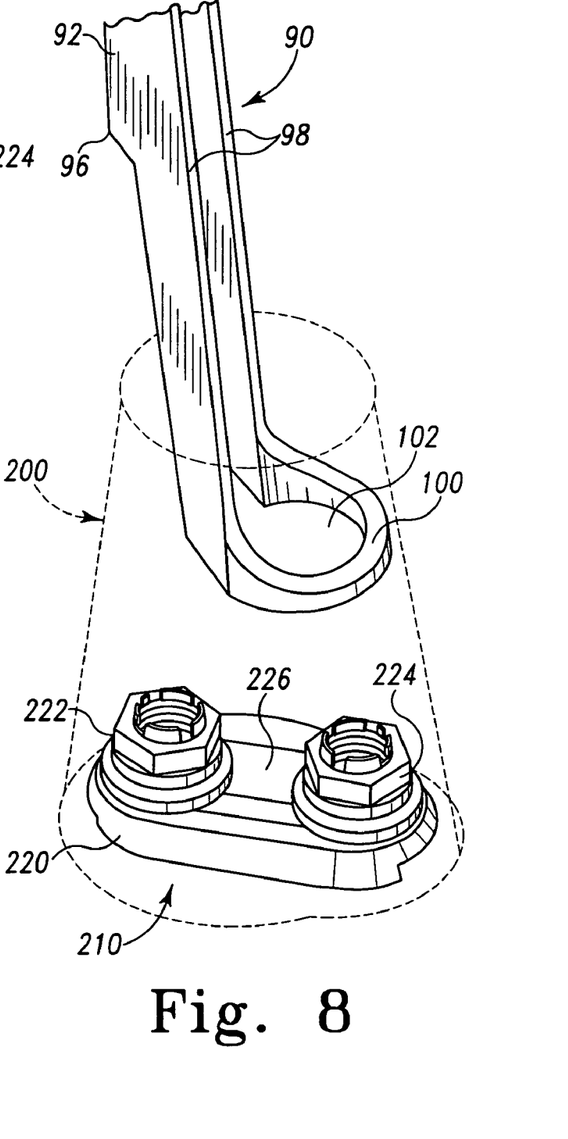
FIG. 8 is a view showing another embodiment compressor being positioned through the portal for mounting with the construct of FIG. 7.
Figures 11, 12:
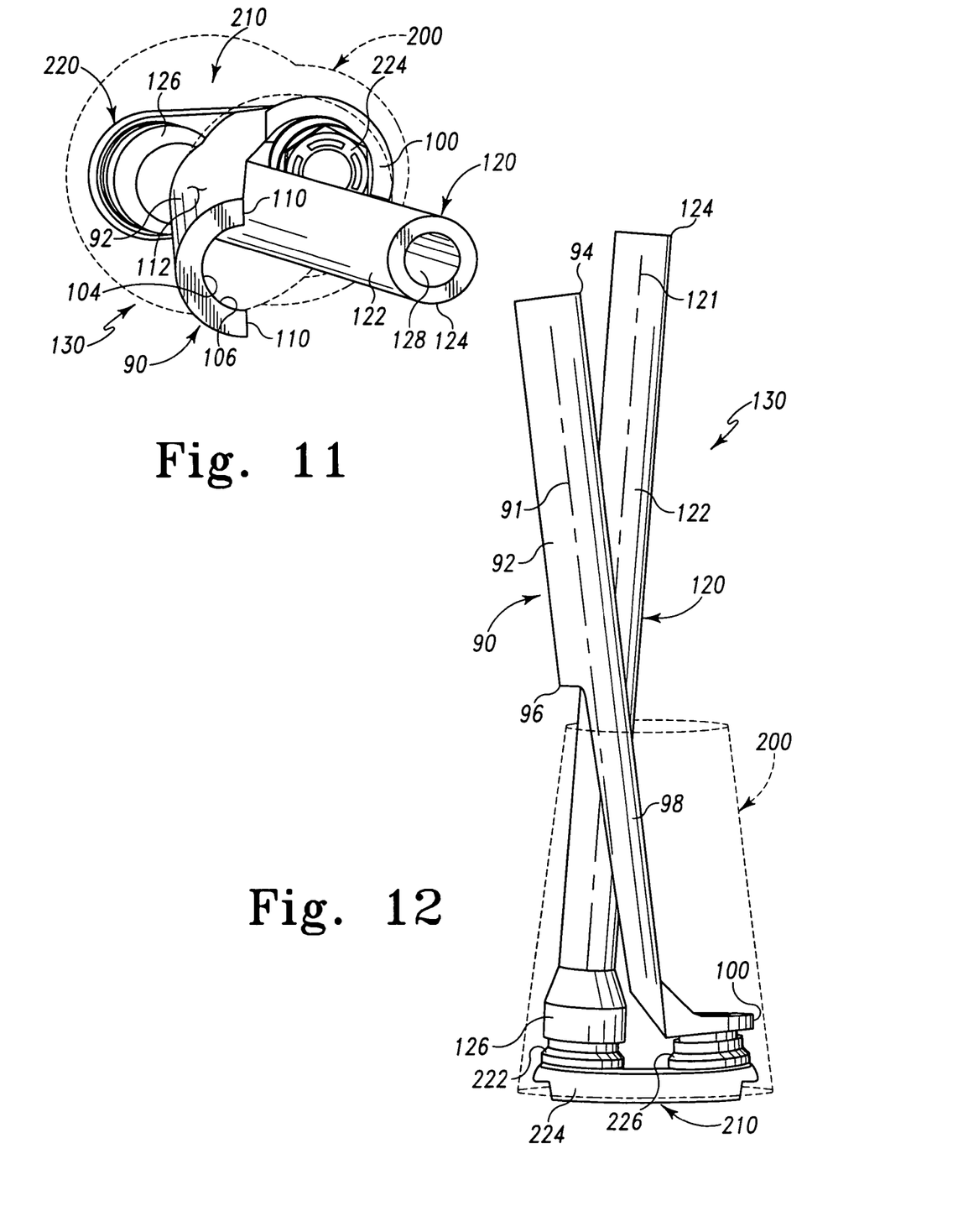
FIG. 11 is a top view showing the compressor and fulcrum through the portal and mounted to the construct of FIG. 7.
FIG. 12 is a view showing the compressor and fulcrum through the portal and mounted to the construct of FIG. 7 before compression of the spinal column.
Figures 13, 14:
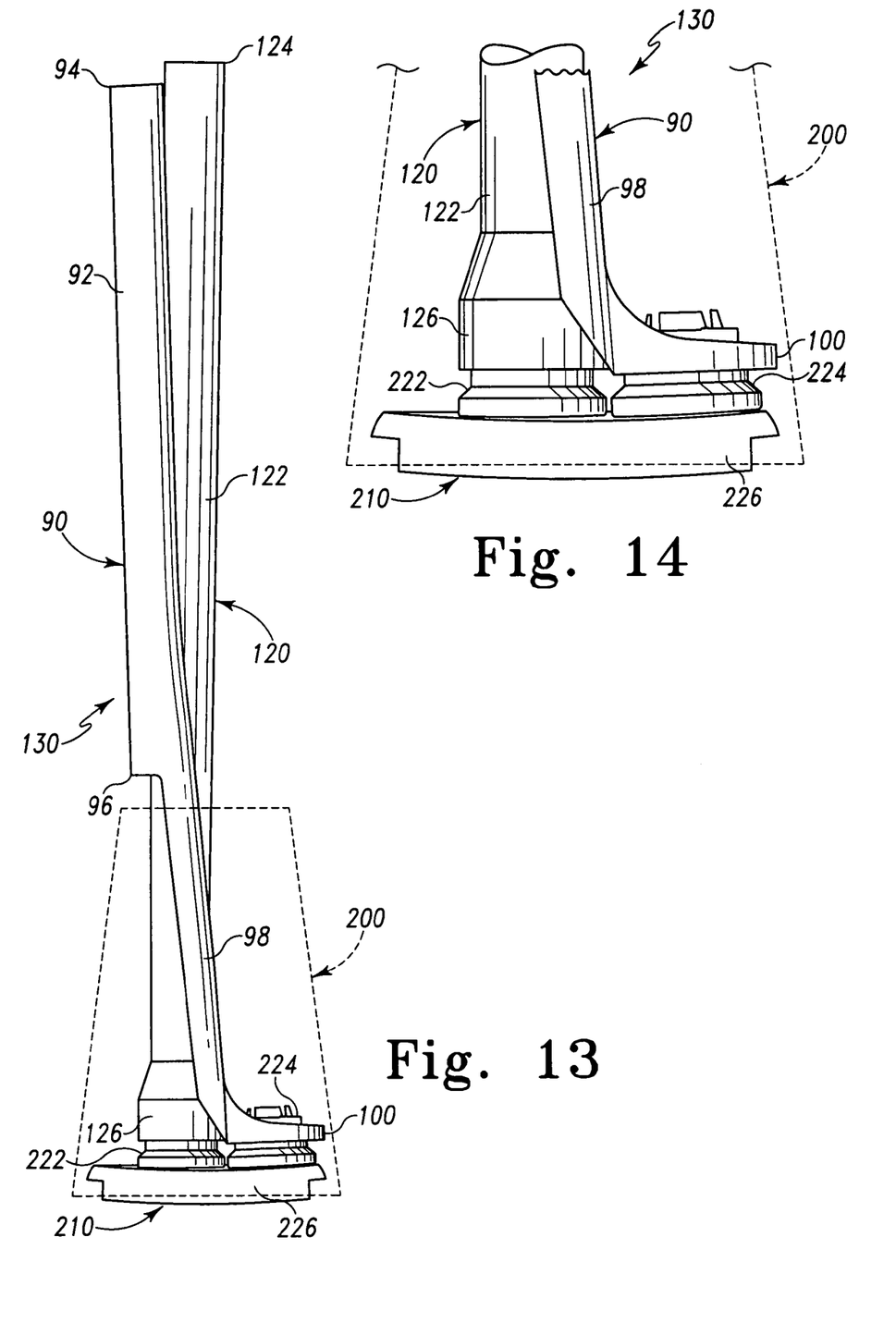
FIG. 13 is a view showing the compressor and fulcrum through the portal and mounted to the construct of FIG. 7 after compression of the spinal column.
FIG. 14 is a view of the construct of FIG. 7 and the distal portions of the fulcrum and compressor mounted thereto after compression of the spinal column.

As shown in FIG. 13, compressor 90 includes an elongated body 92 extending along a longitudinal axis 91 between a proximal end 94 and a distally oriented leverage surface 96. A pair of arms 98 extends distally from body 92, and an engaging member 100 extends between arms 98 at their distal ends. An opening 108 is formed between arms 98 to receive the fulcrum therethrough. As shown in FIG. 8, engaging member 100 extends transversely to arms 98 and forms a receptacle 102 sized and shaped for positioning about the enlarged head of one of the anchors 222, 224. In the illustrated embodiment, receptacle 102 is circular. Other embodiments contemplate other forms and shapes for receptacle 102, including omitting receptacle 102, so long as engaging member 100 is capable of engaging an anchor or a vertebra. As shown in FIG. 11, body 92 defines a channel 104 along one side thereof. Channel 104 can be U-shaped and defined by a concavely curved surface 106 extending between opposite sides 110. A convexly curved outer surface 112 opposite channel 104 facilitates the surgeon grasping compressor 90 during the surgical procedure.

Another embodiment fulcrum 120 is positionable through portal 200 and engageable to the other of the anchors 222, 224. Fulcrum 120 includes an elongate shaft 122 extending between a proximal end 124 and an opposite engaging member 126 at its distal end. As shown in FIG. 11, a passage 128 can extend through shaft 122 and open at its distal and proximal ends. Engaging member 126 includes a profile that receives and engages the second portion of the anchor 222, 224 to which it is mounted. In one embodiment, the second portion of the anchor is a nut or head and engaging member 126 is configured to engage the nut or head to allow rotational forces to be applied to the anchor with fulcrum 120.

Anchors 222, 224 are delivered through portal 200 and engaged to respective ones of the vertebrae, and connecting member 220 is positioned between anchors 222, 224, as shown in FIG. 7. If top-loading anchors 222, 224 are provided, the anchors are engaged to vertebrae 204, 206 before connecting member 220 is delivered and engaged to the anchors. If bottom loading anchors are provided, connecting member 220 is positioned along the vertebrae and anchors 222, 224 are positioned through central opening 226 to engage the connecting member to the vertebrae. In any event, one of the anchors 222, 224 is tightened to securely engage connecting member 220 to the respective vertebra. In the illustrated embodiment, anchor 224 is tightened, while anchor 222 is loosely positioned relative to connecting member 220.

Figures 9, 10:
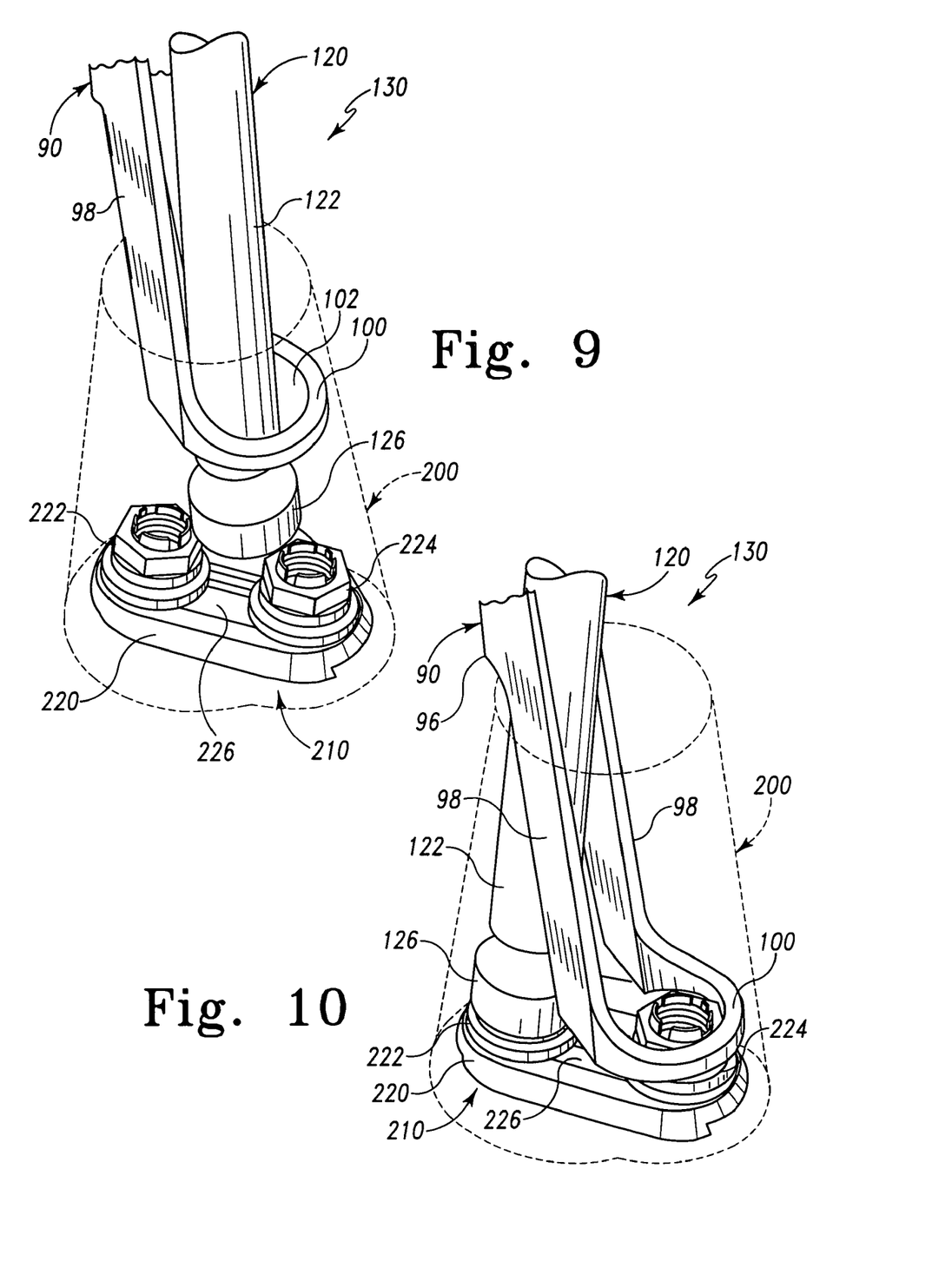
FIG. 9 is a view showing another embodiment fulcrum being positioned through the portal and compressor for mounting with the construct of FIG. 7.
FIG. 10 is a view showing the compressor and fulcrum through the portal mounted to the construct of FIG. 7.

As shown in FIG. 8, compressor 90 is positioned through portal 220 with its engaging member 100 oriented toward anchor 224. In FIG. 9 fulcrum 120 is positioned with its elongated shaft 122 extending through opening 108. Fulcrum 120 and compressor 90 are manipulated in portal 200 so that engaging member 126 is positioned about the second portion of anchor 222, and so that engaging member 100 of compressor 90 is positioned about the second portion of anchor 224. Leverage surface 96 of compressor body 92 is positioned against elongated shaft 122 of fulcrum 120, as shown in FIGS. 10-12. Compressor 90 and fulcrum 110 are oriented relative to one another so that proximal ends 94, 124 are spaced from one another. As shown in FIG. 12, the longitudinal axes 91, 121 of compressor 90 and fulcrum 120 cross one another such that compressor 90 and fulcrum 120 form an X-shape, and distal engaging members 100, 126 are spaced from one another in a direction opposite the spacing of proximal ends 94, 124. Fulcrum 120 is nestably positioned relative to compressor 90 to maintain a low profile footprint for compression system 130 through portal 200, as discussed above with respect to compression system 30.

To compress the vertebrae, proximal ends 94, 124 are moved toward one another, causing compressor 90 and fulcrum 120 to pivot relative to one another about their contact location at leverage surface 96. As the proximal ends 94, 124 move toward one another, the distal engaging members 100, 126 move anchors 222, 224 and thus vertebrae 204, 206 toward one another along connecting member 220. When the desired compression or separation distance between vertebrae 222, 224 has been obtained, anchor 222 can be tightened with fulcrum 120 to secure connecting member 220 between anchors 222, 224. When secured, connecting member 220 maintains the vertebrae in the desired position and with the desired compression attained through use of compression system 130.

A distraction system 160 will be discussed with reference to FIGS. 15-22. Distraction system 160 includes a low profile footprint positionable through portal 200 and engageable to vertebrae to distract the vertebrae relative to one another. Distraction system 160 includes a distractor 140 employed with a fulcrum, such as fulcrum 70 discussed above, which are leveraged off of one another to provide a mechanical advantage in delivering the distraction force to the vertebrae through portal 200.

Figures 15, 16:
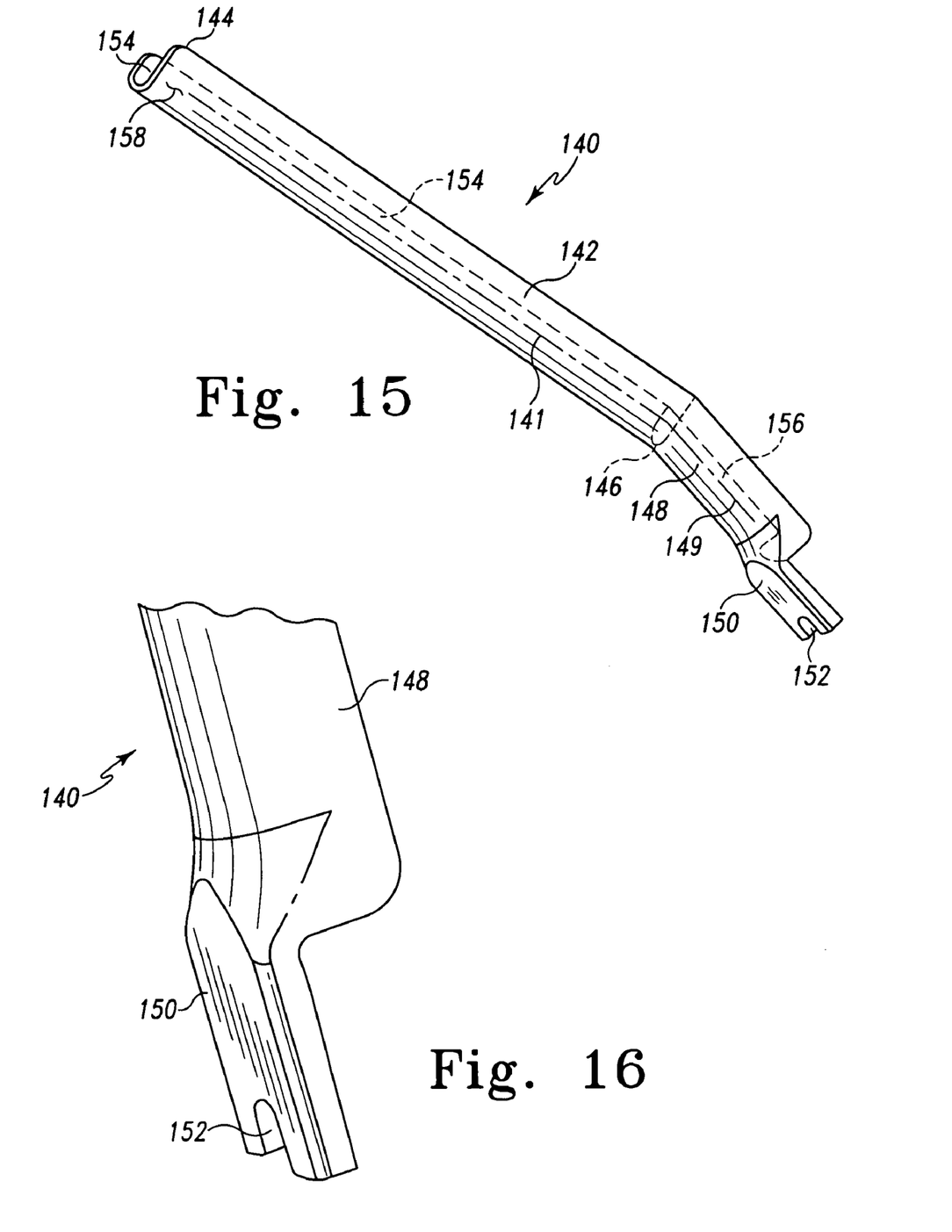
FIG. 15 is a perspective view of a distractor.
FIG. 16 is a view of a distal portion of the distractor.

In FIGS. 15 and 16 there is shown distractor 140 including an elongated body 142 extending along a longitudinal axis 141 between a proximal end 144 and a distal leverage surface 146. An angled distal extension 148 extends distally along longitudinal axis 149 from leverage surface 146 to a distally extending engaging member 150. Longitudinal axis 149 is angled relative to longitudinal axis 141 to angularly offset proximal end 144 from engaging member 150. Engaging member 150 includes a flat, plate-like arm to facilitate positioning between anchors at the surgical site. A distally facing recess 152 is formed in a distal end of engaging member 150.

Body 142 and angled extension 148 include a convexly curved outer surface 158 to facilitate gripping by the surgeon. Opposite outer surface 158 body 142 defines a proximal channel 154, and angled extension 148 defines a distal channel 156. Channels 154, 156 are in communication with one another and extend along respective ones of the longitudinal axes 141, 149 of body 142 and angled extension 148. Channels 154, 156 can be defined by a concavely curved surface as discussed above with respect to compressors 40, 90. Channel 154, 156 can form a U-shaped receptacle sized to receive elongated shaft 72 of fulcrum 70 therein.

Figures 17, 18:
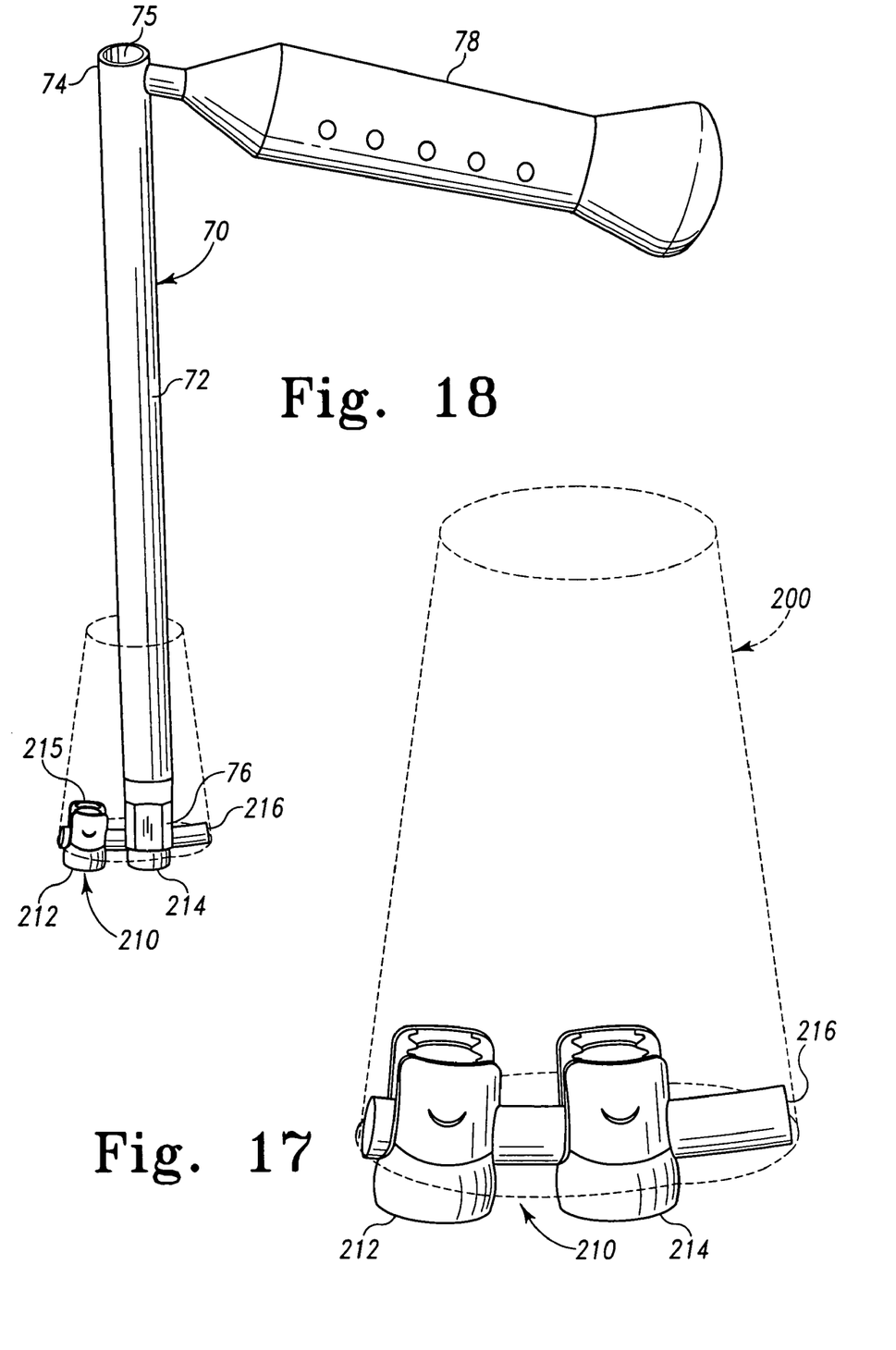
FIG. 17 is a view of a portal and a construct engaged along the spinal column.
FIG. 18 is a view of a fulcrum mounted to the construct of FIG. 17 through the portal.

A construct is positioned through the portal and engaged to vertebrae, such as shown in FIG. 17. In the illustrated embodiment, the construct includes anchors 212, 214 and connecting member 216. Other embodiments contemplate other embodiment constructs as discussed herein. Connecting member 216 is provided with one end protruding from anchor 214 away from anchor 212 to provide a length of connecting member 216 along which anchor 214 can move as the distraction force is applied to the vertebrae.

Figures 19, 20:
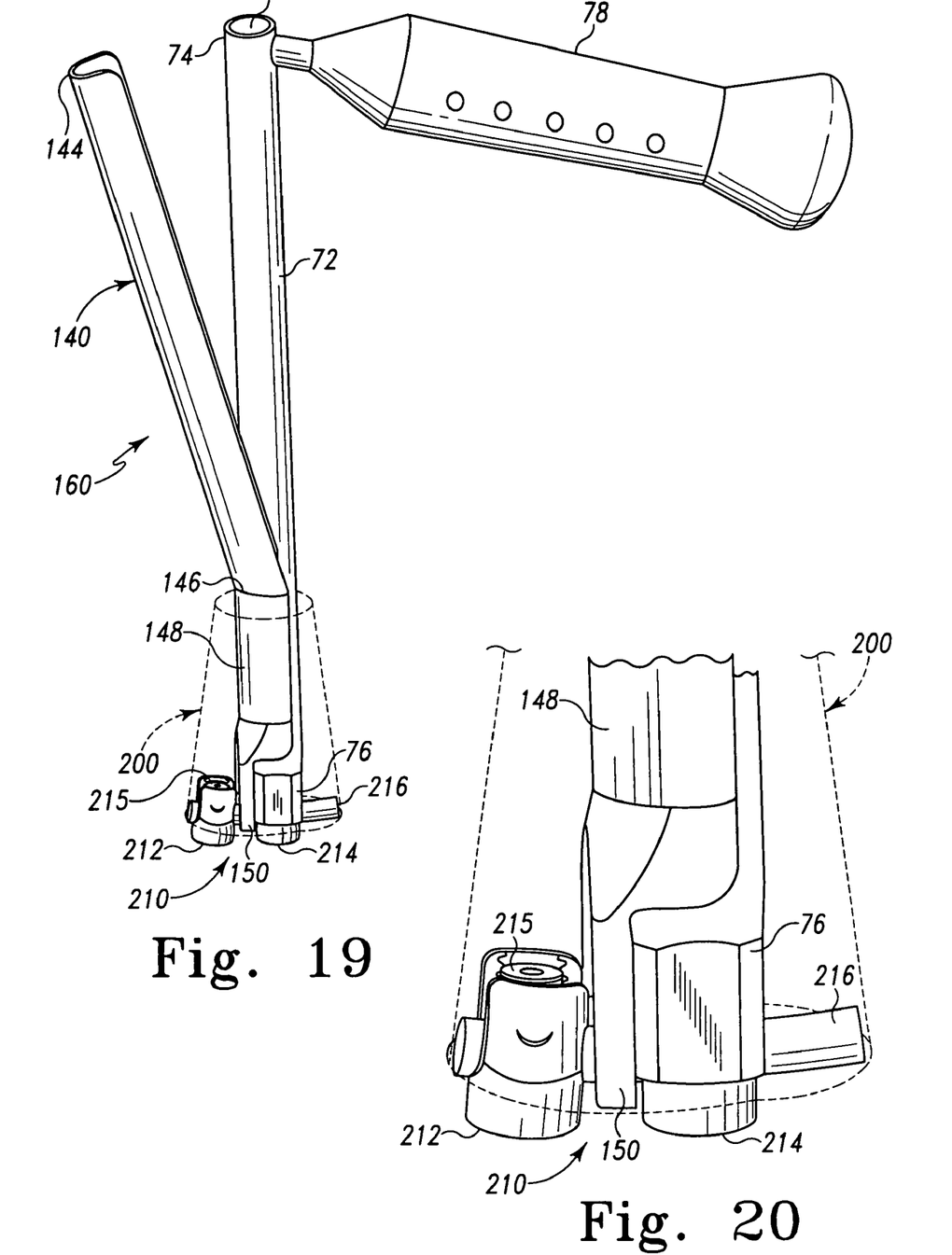
FIG. 19 is a view of the distractor and fulcrum through the portal mounted to the construct of FIG. 17.
FIG. 20 is a view of the distal portions of the distractor and fulcrum mounted to the construct of FIG. 17 before distraction of the spinal column.

A plug 215 can be engaged in anchor 212 to firmly secure connecting member 216 therein, and a plug can be loosely positioned relative to connecting member 216 in anchor 214. In FIG. 18 fulcrum 70 is positioned through portal 200 and its distal engaging member 76 is mounted to anchor 214. In FIG. 19 distractor 140 is positioned through portal 220 so that engaging member 150 is located between anchors 212, 214, and connecting member 216 is received in recess 152. Distal channel 156 is positioned about elongated shaft 72 of fulcrum 70, as shown in FIG. 20. Fulcrum 70 is nestably received relative to distractor 140 to facilitate maintaining the distractor 140 and fulcrum 70 in contact with one another and in alignment during distraction.

In this initial pre-distraction configuration, proximal end 144 of distractor 140 is spaced from proximal end 74 of fulcrum 70, as shown in FIG. 19, due to the angular offset between elongated body 142 and angled extension 148. Leverage surface 146 is located at the junction between proximal channel 154 and distal channel 156 to provide a contact location for distractor 140 against shaft 72 of fulcrum 70. Engaging member 150 is offset away from distal channel 156 so it can be positioned between anchors 212, 214 without interfering with engaging member 76 of fulcrum 70. Leverage surface 146 can be positioned against shaft 72 at any one of a number of locations therealong depending on the separation between anchors 212, 214, the angle of approach to the construct taken with distractor 140 and fulcrum 70, the angle of approach taken with portal 200, and other factors.

Figures 21, 22:
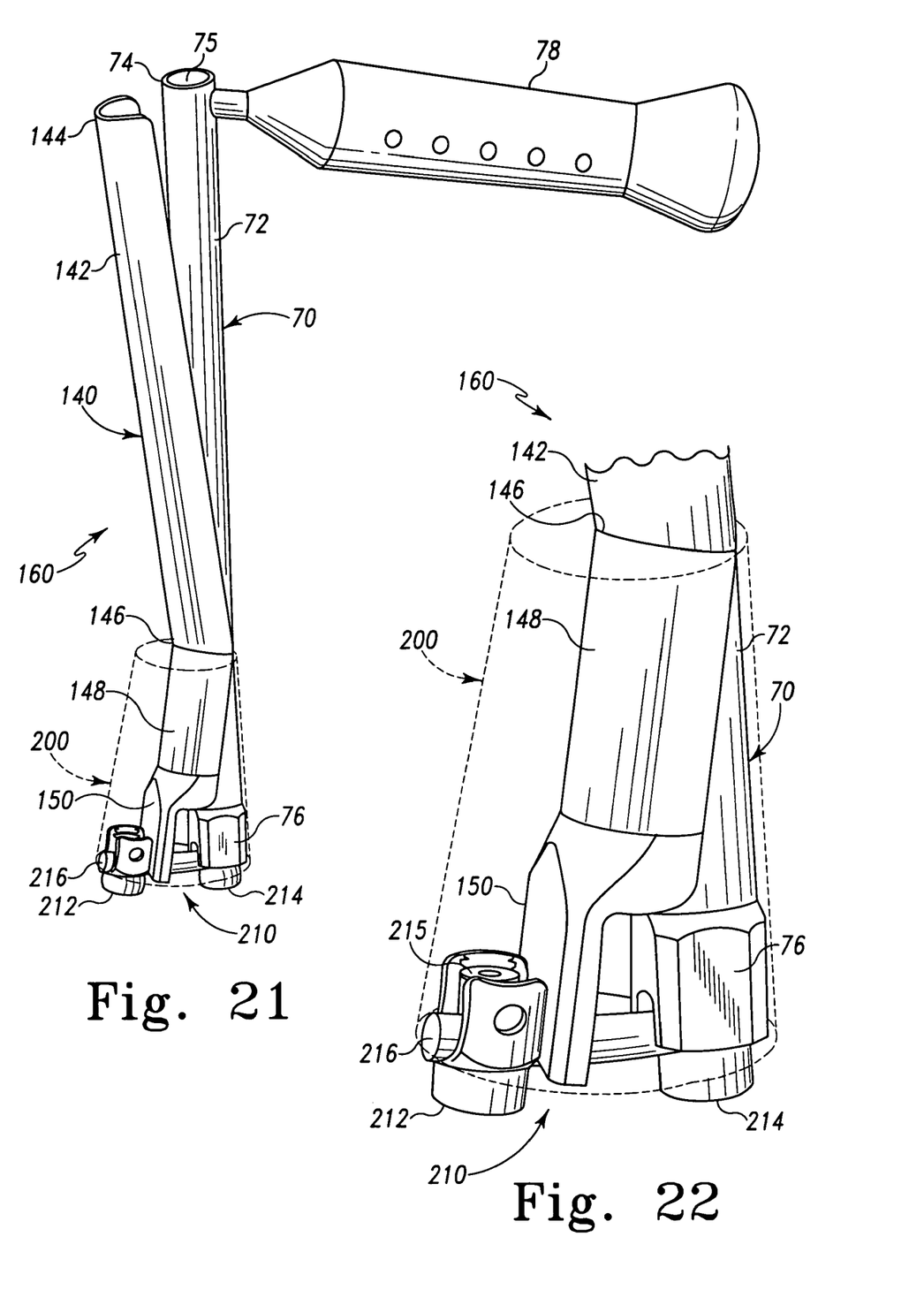
FIG. 21 is a view of the distractor and fulcrum through the portal mounted to the construct of FIG. 17 after distraction of the spinal column.
FIG. 22 is an enlarged view of the distal portions of the distractor and fulcrum mounted to the construct after distraction of the spinal column.

To distract the vertebrae, proximal end 144 of distractor 140 is moved from its initial configuration toward proximal end 74 of fulcrum 70, as shown in FIG. 21. Distractor 140 pivots relative to fulcrum 70 about leverage surface 146 to move engaging member 150 and engaging member 76 away from one another as further shown in FIG. 22. This movement causes anchor 214 to slide along connecting member 216 as the vertebrae are distracted. When the desired distraction has been obtained, a driving tool can be positioned through passage 75 of fulcrum 70 to secure the plug in anchor 214 against connecting member 216 to post-operatively maintain the distraction of the vertebrae.

While the invention has been illustrated and described in detail in the drawings and foregoing description, the same is to be considered as illustrative and not restrictive in character, and that all changes and modifications that come within the spirit of the invention are desired to be protected.

What is claimed is:

1. A compressor, comprising:
   an elongated body extending between a proximal end and a distal leverage surface, said elongated body including a channel extending at least partially between said proximal end and distal leverage surface;
   a pair of arms extending distally of said distal leverage surface of said body, said pair of arms defining an elongated opening therebetween for receiving a fulcrum therethrough; and
   an engaging member extending between distal ends of said pair of arms, said engaging member being mountable to an anchor engaged to a bony portion of a patient's body, said engaging member includes a pair of extensions extending transversely to respective ones of said pair of arms and an end member extending between said pair of extensions, said end member and said pair of extensions being arranged to accommodate a bone anchor therebetween and said end member including a distally oriented recess extending therein to receive a connecting element extending from the bone anchor when the bone anchor is positioned between said pair of extensions, wherein said opening extends between said engaging member and said distal leverage surface of said elongated body.

2. The compressor of claim 1, wherein said engaging member defines a circular receptacle.

3. The compressor of claim 1, wherein said engaging member defines a rectangular receptacle.

4. The system of claim 1, wherein said channel is defined by a concavely curved surface extending between opposite sides of said elongated body.

5. A spinal surgical system, comprising:
   a compressor engageable to a first vertebra, said compressor including an elongated body extending between a proximal end and a distal leverage surface, a pair of arms extending distally of said distal leverage surface of said body and defining an opening therebetween, and an engaging member at a distal end of said arms extending from one of said pair of arms to the other of said pair of arms; and
   a fulcrum including an elongated shaft extending between a proximal end and a distal end, said distal end being engageable to a second vertebra, said distal end of said fulcrum being sized for positioning through said opening between said arms of said compressor and said opening of said compressor is arranged to receive an anchor engaged to the first vertebra to position said engaging member in engagement with the anchor while said distal end of said fulcrum extends through said opening and is engaged to an anchor engaged to the second vertebra, wherein said compressor is movable along a length of said elongated shaft between said proximal and distal ends of said elongated shaft to proximally and distally vary a location in which said distal leverage pivots against said elongated shaft in accordance with a relative positioning between said distal ends of said compressor and said fulcrum, said compressor and said fulcrum having a first configuration wherein said distal leverage surface contacts said elongated shaft of said fulcrum with said distal end of said fulcrum positioned to a first side of said engaging member of said compressor and said proximal end of said fulcrum positioned to a second side of said proximal end of said compressor, said second side being opposite said first side, wherein movement of said proximal ends of said compressor and said fulcrum toward one another when said engaging member is engaged to the first vertebra and said distal end of said fulcrum is engaged to the second vertebra moves said engaging member of said compressor and said distal end of said fulcrum toward one another about said distal leverage surface to compress the first and second vertebrae.

6. The system of claim 5, wherein said elongated body of said compressor and said elongated shaft of said fulcrum cross one another in said first configuration to form an X shape.

7. The system of claim 5, wherein said elongated body of said fulcrum extends along a longitudinal axis and said fulcrum includes a handle extending from said proximal end transversely to said longitudinal axis.

8. The system of claim 7, wherein said handle is orthogonal to said longitudinal axis.

9. The system of claim 5, wherein said fulcrum includes a passage extending through said elongated shaft, said passage opening at said distal and proximal ends of said fulcrum.

10. The system of claim 5, wherein said elongated body of said compressor includes a channel between said proximal end and said distal leverage surface, said channel being oriented toward said elongated shaft of said fulcrum in said first configuration.

11. The system of claim 10, wherein said channel is formed by a concave surface extending between opposite sides of said elongated body of said compressor.

12. The system of claim 10, wherein in said first configuration said elongated shaft is positioned in a portion of said channel in contact with said distal leverage surface of said elongated body of said compressor.

13. The system of claim 12, wherein in use at least one of said compressor and said fulcrum are moveable relative to the other from said first configuration to a second configuration to deliver a compression force between the first and second vertebrae by pivoting said at least one of said fulcrum and said compressor about said distal leverage surface.

14. The system of claim 13, wherein said pivoting of said at least one of said compressor and said fulcrum includes positioning said elongated shaft of said fulcrum in said channel of said compressor.

15. A spinal surgical system, comprising:
a compressor engageable to a first vertebra, said compressor including an elongated body extending between a proximal end and a distal leverage surface, a pair of arms extending distally of said distal leverage surface of said body and defining an opening therebetween, and an engaging member at a distal end of said arms extending between said arms; and
a fulcrum including an elongated shaft extending between a proximal end and a distal end, said distal end being engageable to a second vertebra, said distal end of said fulcrum being sized for positioning through said opening between said arms of said compressor and said opening of said compressor is arranged to receive an anchor engaged to the first vertebra to position said engaging member in engagement with the anchor while said distal end of said fulcrum extends through said opening and is engaged to an anchor engaged to the second vertebra, wherein said compressor is movable along a length of said elongated shaft between said proximal and distal ends of said elongated shaft to proximally and distally vary a location in which said distal leverage pivots against said elongated shaft in accordance with a relative positioning between said distal ends of said compressor and said fulcrum, said compressor and said fulcrum having a first configuration wherein said distal leverage surface contacts said elongated shaft of said fulcrum with said distal end of said fulcrum positioned to a first side of said engaging member of said compressor and said proximal end of said fulcrum positioned to a second side of said proximal end of said compressor, said second side being opposite said first side, wherein movement of said proximal ends of said compressor and said fulcrum toward one another when said engaging member is engaged to the first vertebra and said distal end of said fulcrum is engaged to the second vertebra moves said engaging member of said compressor and said distal end of said fulcrum toward one another about said distal leverage surface to compress the first and second vertebrae, wherein said engaging member of said compressor includes a pair of extensions extending transversely to respective ones of said pair of arms and an end member extending between said pair of extensions.

16. The system of claim 15, wherein said engaging member defines a circular receptacle.

17. The system of claim 15, wherein said engaging member defines a rectangular receptacle.

18. The system of claim 15, wherein said engaging member includes a distally oriented recess therein.

19. A spinal surgical system, comprising:
a compressor engageable to a first vertebra, said compressor including an elongated body extending between a proximal end and a distal leverage surface, a pair of arms extending distally of said distal leverage surface of said body and defining an opening therebetween, and an engaging member at a distal end of said arms extending between said arms; and
a fulcrum including an elongated shaft extending between a proximal end and a distal end, said distal end being engageable to a second vertebra, said distal end of said fulcrum being sized for positioning through said opening between said arms of said compressor and said opening of said compressor is arranged to receive an anchor engaged to the first vertebra to position said engaging member in engagement with the anchor while said distal end of said fulcrum extends through said opening and is engaged to an anchor engaged to the second vertebra, wherein said compressor is movable along a length of said elongated shaft between said proximal and distal ends of said elongated shaft to proximally and distally vary a location in which said distal leverage pivots against said elongated shaft in accordance with a relative positioning between said distal ends of said compressor and said fulcrum, said compressor and said fulcrum having a first configuration wherein said distal leverage surface contacts said elongated shaft of said fulcrum with said distal end of said fulcrum positioned to a first side of said engaging member of said compressor and said proximal end of said fulcrum positioned to a second side of said proximal end of said compressor, said second side being opposite said first side, wherein movement of said proximal ends of said compressor and said fulcrum toward one another when said engaging member is engaged to the first vertebra and said distal end of said fulcrum is engaged to the second vertebra moves said engaging member of said compressor and said distal end of said fulcrum toward one another about said distal leverage surface to compress the first and second vertebrae, and further comprising:
a construct including an elongated connecting member extending between the first and second vertebrae and the first and second anchors for engaging the connecting member to respective ones of the first and second vertebrae, wherein said compressor and said fulcrum are mountable to respective ones of the first and second anchors.

20. The system of claim 19, wherein said connecting member is a plate, said first anchor and said second anchor each include a first portion engageable to respective ones of the first and second vertebrae and a second portion engaged to said first portion to secure said plate to said respective anchor, said engaging member of said compressor being positionable about said second portion of said first anchor and said fulcrum including an engaging member at said distal end thereof positionable about said second portion of said second anchor.

21. The system of claim 20, wherein said plate includes a central slot for receiving said first portions of said first and second anchors therethrough, at least one of said first and second anchors being movable along said central slot of said plate as said engaging members of said compressor and said fulcrum are moved toward one another about said distal leverage surface.

22. The system of claim 19, wherein said connecting member is a rod, said first anchor and said second anchor each include a first portion engageable to respective ones of the first and second vertebrae and a second portion extending proximally from said first portion to receive said rod and a plug for engaging said rod to said second portion, said compressor being positionable about said second portion of said first anchor and said fulcrum including an engaging member at a distal end thereof positionable about said second portion of said second anchor.

23. The system of claim 22, wherein at least one of said first and second anchors is movable along said rod as said engaging members of said compressor and said fulcrum are moved toward one another to compress the first and second vertebrae.

24. A spinal surgical system, comprising:
a compressor including an elongated body extending between a proximal end and a leverage surface, said compressor further including an engaging member spaced distally of said leverage surface and an opening between said leverage surface and said engaging member, said opening being arranged to receive an anchor engageable to a first vertebra; and
a fulcrum including an elongated shaft extending between a proximal end and a distal end, said distal end being engageable to a second vertebra, said distal end of said fulcrum being sized for positioning through said opening while said opening of said compressor receives the anchor engaged to the first vertebra to position said engaging member in engagement with the anchor and said fulcrum being removably and nestably received relative to said compressor when said distal end of said fulcrum extends through said opening and is engaged to the second vertebra, wherein said compressor is movable along a length of said elongated shaft between said proximal and distal ends of said elongated shaft to proximally and distally vary a location in which said leverage surface pivots against said elongated shaft in accordance with a relative positioning of said distal end of said fulcrum relative to said engaging member of said compressor, said compressor and said fulcrum having a first configuration wherein said leverage surface contacts said elongated shaft and said distal end of said fulcrum is positioned to a first side of said engaging member of said compressor and said proximal end of said fulcrum is positioned to a second side of said proximal end of said compressor, said second side being opposite said first side, wherein movement of said proximal ends of said compressor and said fulcrum toward one another moves said engaging member of said compressor and said distal end of said fulcrum toward one another to compress the first and second vertebrae; and
a construct including an elongated connecting member extending between the first and second vertebrae and first and second anchors for engaging the connecting member to respective ones of the first and second vertebrae, wherein said compressor and said fulcrum are mountable to respective ones of the first and second anchors, said elongated connecting member being movable along at least one of said anchors when said proximal ends of said fulcrum and said compressor are moved toward one another to move said engaging member of said compressor and said distal end of said fulcrum toward one another to compress the first and second vertebrae.

25. The system of claim 24, further comprising a pair of arms extending from said leverage surface of said body and defining said opening therebetween, said engaging member extending between said pair of arms at a distal end of said arms and said leverage surface extending between said pair of arms at a proximal end of said pair of arms.

26. The system of claim 25, wherein said fulcrum is received through said opening between said pair of arms.

27. The system of claim 24, wherein said elongated body of said compressor and said elongated shaft of said fulcrum cross one another in said first configuration to form an X shape.

28. The system of claim 24, wherein said elongated shaft of said fulcrum extends along a longitudinal axis and said fulcrum includes a handle extending from said proximal end transversely to said axis.

29. The system of claim 24, wherein said elongated body of said compressor includes a channel extending at least partially between said proximal end distal ends thereof oriented toward said elongated shaft of said fulcrum in said first configuration.

30. A method for compressing vertebrae, comprising:
positioning a compressor through a portal to the vertebrae;
positioning a distal end of a fulcrum through an opening of the compressor with the compressor positioned through the portal;
mounting an engaging member of the compressor to a first vertebra, the compressor extending from the engaging member to an opposite proximal end;
mounting the distal end of the fulcrum to a second vertebra, the fulcrum extending from the distal end to an opposite proximal end;
positioning the fulcrum against a leverage surface of the compressor after mounting the distal end of the fulcrum to the second vertebra, wherein the leverage surface contacts the fulcrum with the distal end of the fulcrum positioned to a first side of the engaging member of the compressor and the proximal end of the fulcrum is positioned to a second side of the proximal end of the compressor, the second side being opposite the first side; and
pivoting the compressor and fulcrum relative to one another about the leverage surface by moving proximal ends of the compressor and fulcrum toward one another to move distal ends of the compressor and fulcrum toward one another, thereby compressing the vertebrae.

31. The method of claim 30, wherein the leverage surface is positionable at any one of a number of locations along the fulcrum.

32. The method of claim 30, wherein positioning the fulcrum against the leverage surface of the compressor includes positioning the fulcrum in the opening between a pair of arms extending distally from the leverage surface with the fulcrum and compressor crossing one another to form an X shape.

33. The method of claim 30, wherein pivoting the compressor and fulcrum relative to one another includes positioning the fulcrum in a channel extending along the compressor from the leverage surface to the proximal end of the compressor.

34. The method of claim 30, wherein mounting the compressor and mounting the fulcrum each include mounting the compressor and mounting the fulcrum to an anchor engaged to respective ones of the first and second vertebrae with the fulcrum and compressor crossing one another to form an X shape, wherein the anchor mounted to the compressor is received in the opening of the compressor.

35. The method of claim 30, further comprising engaging a connecting member between the first and second anchors when a desired compression between the first and second vertebrae is obtained.

* * * * *